United States Patent [19]

Wildt et al.

[11] Patent Number: 5,146,039

[45] Date of Patent: Sep. 8, 1992

[54] PROCESS FOR LOW LEVEL DESULFURIZATION OF HYDROCARBONS

[75] Inventors: Thomas Wildt, Essen; Franz Nierlich, Marl; Wilhelm Droste, Marl; Joachim Neumeister, Marl; Bernhard Scholz, Marl-Polsum, all of Fed. Rep. of Germany

[73] Assignee: Huels Aktiengesellschaft, Marl, Fed. Rep. of Germany

[21] Appl. No.: 608,623

[22] Filed: Nov. 6, 1990

Related U.S. Application Data

[63] Continuation of Ser. No. 376,616, Jul. 7, 1989, abandoned.

[30] Foreign Application Priority Data

Jul. 23, 1988 [DE] Fed. Rep. of Germany ....... 3825169

[51] Int. Cl.$^5$ ................................................. C07C 7/13
[52] U.S. Cl. .................................... 585/820; 423/244; 55/74; 208/310 Z
[58] Field of Search ................ 423/230; 502/400, 517; 585/820; 55/73, 74; 208/310 Z

[56] References Cited

U.S. PATENT DOCUMENTS

| | | | |
|---|---|---|---|
| 4,358,297 | 11/1982 | Eberly, Jr. ............................. | 55/73 |
| 4,533,529 | 8/1985 | Lee ....................................... | 423/230 |
| 4,556,547 | 12/1985 | Nishino et al. ...................... | 423/231 |
| 4,673,557 | 6/1987 | Nieskens et al. .................... | 423/230 |
| 4,786,483 | 11/1988 | Audeh .................................. | 423/230 |
| 4,798,813 | 1/1989 | Kato et al. ........................... | 502/60 |
| 4,830,733 | 5/1989 | Nagji et al. .......................... | 502/20 |
| 4,830,734 | 5/1989 | Nagji et al. .......................... | 585/822 |

Primary Examiner—Anthony McFarlane
Attorney, Agent, or Firm—Oblon, Spivak, McClelland, Maier & Neustadt

[57] ABSTRACT

A hydrocarbon containing sulfides, disulfides, trisulfides, tetrasulfides or mixtures can be desulfurized by contacting the hydrocarbon with a zeolite containing copper, silver, zinc or mixtures thereof.

9 Claims, 3 Drawing Sheets

PROCESS FOR LOW LEVEL DESULFURIZATION OF HYDROCARBONS

BACKGROUND OF THE INVENTION

1. Field of the Invention

The present invention relates to a process for the low level desulphurization of hydrocarbons containing sulfides, disulfides, trisulfides or tetrasulfides or mixtures thereof.

2. Description of the Background

It is generally known that sulfur compounds act as catalyst poisons, in particular for catalysts containing transition metals of group VIII. Because of their frequently unpleasant odors, and because they are frequently found in hydrocarbons such as in propane and butanes which are used to an increasing extent in aerosol technology, the removal of such sulfur compounds from such materials is desired. In this context even sulfur contents far below 0.1 ppm may still give an unpleasant odor.

The removal of di-, tri- and higher oligosulfides is particularly important, because many petrochemically recovered hydrocarbons contain such compound(s) as a result of their preliminary purification, for instance, the processing of hydrocarbons by the Merox process as described in EP-A 0 235 462.

It is known that sulfides and disulfides can be removed from substances by adsorption. Adsorbents which have been used frequently for this purpose include activated charcoal, zeolites and porous silicates. N. Gryazev et al describe the adsorption of sulfides and disulfides from solutions on zeolites, silica gel and aluminum silicates (Khim. Seraorg. Soedin. Soderzh. Neft. Nefteprod., 9 (1972), 415–420). S. Tanada and K. Boki similarly investigated the removal of sulfur compounds on zeolites and silicates and in addition also studied the adsorption of dimethylsulfide on activated charcoal (Tokushima Bunri Daigaku Kenkyo Kiyo, 15 (1976), 33–38).

I. P. Muklenov et al. have shown that dimethyl sulfide and dimethyl disulfide in addition to other compounds can be removed from waste gases by adsorption on activated charcoal (Bum. Prom.-st. 7 (1978), 27–28). Further, N. A. Sankhin et al., Bum. Prom-st. 11 (1979), 27–28, have shown the adsorption of dimethyl sulfide and dimethyl disulfide and in addition other sulfur compounds on activated charcoal, which compounds are produced during the manufacture of sulfates.

T. Suetaka and M. Munemori have also described the adsorption of sulfides, more particularly the adsorption of dimethyl sulfide and diethyl sulfide, on activated charcoal [Akushu no Kenkyn 18, 72 (1987), 32 –34.

Shcherbina et al. in Obshch. Prikl. Khim., No. 5 (1972), 113–114, have described the adsorption of sulfur compounds on sodium zeolites of the X-type, while Mikhal'skaya et al., Khim. Tekhol. 9 (1975), 64 –66 have shown the adsorption of sulfur compounds on sodium zeolites of the Y type. Disulfides as well as mercaptans can be removed from hydrocarbons by means of sodium zeolites of the X type, whereas with sulfides this is stated to take place only incompletely.

JP-OS 59/160 584 describes the adsorption of disulfides and sulfides in addition to H2S, COS and mercaptans on activated charcoal containing heavy metals.

In addition it is known from DD-PS 241 196 and DD-PS 241 197 that hydrogen sulfide and organic sulfur compounds can be removed from carbon dioxide-containing gas mixtures by adsorption on zinc and manganese zeolites of the X type. Using this type of adsorbent DD-PS 241 196 discloses a process for preventing the formation of carbon oxysulfide in desulfurization processes and DD-PS 241 197 in sorptive separation processes. The objective in these processes is to reduce the loss of sulfur as a result of carbon oxysulfide formation having regard to the downstream production of elemental sulfur. However, both processes can be carried out only in the very limited temperature range of 10° to 50° C. Further, DD-PS 241 197 shows that it is possible to thermally regenerate zeolites loaded with sulfur compounds.

None of the processes shown to date for the adsorption of sulfides and disulfides are suitable for the low level desulfurization of hydrocarbons. A need therefore continues to exist for a method of effectively desulfurizing hydrocarbons.

SUMMARY OF THE INVENTION

Accordingly, one object of the invention is to provide a process for the low level desulfurization of hydrocarbons which contain sulfides, disulfides, trisulfides, tetrasulfides and further polysulfides.

Briefly, this object and other objects of the present invention as hereinafter will become more readily apparent can be attained by a process for desulfurizing a hydrocarbon material by contacting a sulfide, disulfide, trisulfide, tetrasulfide or polysulfide containing hydrocarbon with a copper, silver and/or zinc containing zeolite.

By implementation of the process of the present invention it has been found possible to achieve desulfurization of hydrocarbons far above 90% even with hydrocarbons having a very low initial content of sulfur.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
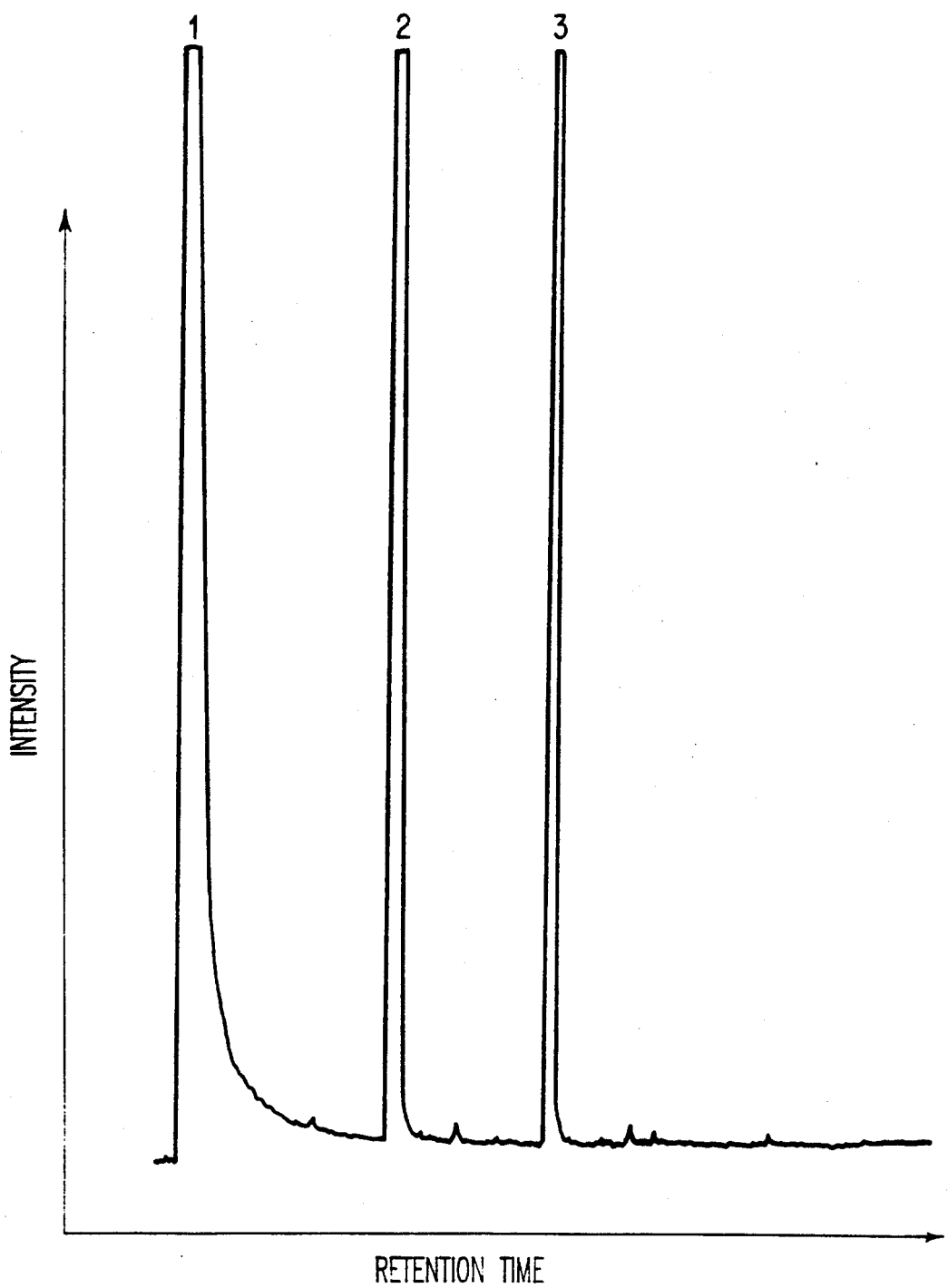
FIG. 1 is a gas chromatogram of a propene/propane starting material containing sulfide materials.

The term low level desulfurization means the desulfurization of hydrocarbons containing less than 20 ppm by weight of sulfur, preferably less than 10 ppm by weight of sulfur.

According to the present invention it has been found possible to achieve desulfurization degrees far beyond 90% even with hydrocarbons having a very low starting content of sulfur. By means of the process of the present invention it is even possible to desulfurize hydrocarbons, having an appropriate starting content of sulfur, down to residual contents below 5 ppb S.

Preferably, the hydrocarbon starting material to be desulfurized to a low level contains 1 to 20 carbon atoms.

The process of the present invention can be carried out both in the gas phase as well as in the liquid phase, either continuously or discontinuously.

The zeolite adsorbent used in the present invention may be prepared for example, by a procedure in which the exchangeable cations of a zeolite are wholly or in part exchanged with cations of the metals copper, silver or zinc or combinations thereof. Suitable zeolite materials which can be ion exchanged include zeolites of type A, X or Y. Exchangeable cations of the starting zeolite include, for example, alkali metal and/or ammonium cations.

Preferably the content of the zeolite in the present invention with respect to copper, silver or zinc respectively amounts to at least 2% by weight.

In order to prepare the exchanged zeolite of the invention a continuous process can be employed in which a starting zeolite is placed in column and an organic or an aqueous solution of copper, silver or zinc salts or combinations thereof and/or complexes thereof is allowed to flow through the column. On the other hand, a discontinuous ion exchange process may be employed in which a starting zeolite is added to and shaken in a metal ion containing solution. Preferably, the ion exchange takes place at a pH of 5 to 12, a matter depending inter alia on the stability of the zeolite selected. Temperatures suitable for the exchange process are in the range from 20° to 80° C., the exchange period varying from several minutes up to several hours. Preferred concentrations of the solution containing copper, silver or zinc or combinations thereof are in the range of 0.1 to 10 mol per liter and preferred particle sizes of the zeolites are from 0.01 to 5 mm.

After the exchange has taken place, weakly adsorbed copper, silver and/or zinc salts and/or complexes thereof may be removed from the zeolite by extraction with a suitable solvent, such as, e.g., water or an alcohol.

The exchanged zeolite is dried at about 100 to 200° C. and subsequently treated thermally at about 200 to 600° C.

The complete zeolite containing copper, silver or zinc or combinations thereof is usable for the continuous, as well as for the discontinuous low level desulfurization of hydrocarbons. The process of the invention can be carried out in the gas or liquid phase at temperatures of 50° to 350° C., preferably of 50° to 130° C., and at pressures of 1 to 200 bar, preferably of 1 to 50 bar.

Moreover, the process of the invention, may be carried out continuously at a "weight hourly space velocity"

$$\left( WHSV = \frac{\text{amount of starting material}}{\text{amount of zeolite} \cdot \text{time}} \left[ \frac{kg}{kg \cdot h} \right] \right)$$

of 0.05 to 100 $h^{-1}$, preferably of 1 to 40 $h^{-1}$.

The process conditions are selected within the above limits in the first instance having regard to the economics of the process. Thus, for example the WHSV determines the shape of the break-through curve and thereby also the utilization of the zeolite bed down to a breakthrough concentration of sulfur compounds which can still be tolerated.

Having generally described this invention, a further understanding can be obtained by reference to certain specific examples which are provided herein for purposes of illustration only and are not intended to be limiting unless otherwise specified.

The sulfur contents of various hydrocarbon materials were determined by gas chromatography, a flame photometric detector and a chromatographic column packed with CP-Sil 5 ® (Chrompak).

All percentage data are in terms of weight %. The same applies to data in terms of ppm and ppb.

EXAMPLE 1

A 500 g amount of sodium zeolite of type X was mixed with 750 ml of a 1 molar $ZnCl_2$ solution, the pH value of which had previously been adjusted to 5 with conc. hydrochloric acid. The suspension was agitated for 24 h at 80° C., the zeolite was then dried at 100° C. and thereafter thermally treated at 300° C. The Zn content of the zeolite amounted to 6.23%.

n-Butane having a starting content of 60 pph sulfur in the form of dimethyl disulfide was desulfurized for 48 h continuously at a WHSV of 0.75 $h^{-1}$ and a temperature of 100° C. at a pressure of 20 bar on the above described Zn zeolite down to a residual content of less than 5 ppb S.

EXAMPLE 2 n-Butane, contaminated with 150 ppb S in the form of dimethyl disulfide, was passed continuously at a WHSV of 4 $h^{-1}$ for 4 days at a temperature of 120° C. and a pressure of 50 bar over a copper zeolite of type Y having a Cu content of 4.5% which had been produced as described above in Example 1. Even after 4 days the sulfur content of the n-butane was still below the detection limit of 5 ppb S.

EXAMPLE 3

The test was carried out analogously to that described in Example 2 at a pressure of 9 bar. In this case as well, n-butane was desulfurized down to a sulfur content of less than 5 ppb S.

EXAMPLE 4

A copper zeolite of type X having a Cu content of 5.1% was produced analogously to that of Example 1 and tested at the conditions specified in Example 2. In this case as well, it was possible to desulfurize the n-butane down to a sulfur content of less than 5 ppb S.

EXAMPLE 5 n-Butane having a dimethyl disulfide content calculated as 2 ppm S was desulfurized at a WHSV of 3,75 $h^{-1}$ a temperature of 120° C. and a pressure of 30 bar for 2 days continuously on a copper zeolite of type X having a Cu content of 10%, produced in a manner analogous to that described in Example 1, down to a residual content of 20 ppb S.

EXAMPLE 6 n-Butane contaminated with 500 ppb S in the form of methyl-2-butyl sulfide, was passed at a WHSV of 1.5 $h^{-1}$ at a temperature of 60° C. at a pressure of 20 bar over a zeolite of type X produced analogously to the procedure described in Example 1 and containing 6% Zn and 4% Cu. After a running period of 48 h a desulfurization down to 43 ppb S had been attained.

EXAMPLE 7

A mixture of $C_{20}$ olefins (butene pentameres) was desulfurized in a manner analogous that described in Example 6. The residual content of sulfur amounted to 32 ppb S.

EXAMPLE 8

A zeolite of type X, manufactured in a manner analogous to that described in Example 1 with an Ag content of 10% and a Cu content of 2%, was employed at a WHSV of 1.5 $h^{-1}$ at a temperature of 130° C. at a pressure of 5 bar to desulfurize n-butane having a sulfur content of 2 ppm S in the form of methyl-1-butylsulfide (50%) and methyl-2-butylsulfide (50%). After a running period of 36 hours the sulfur content of the n-butane was only 27 ppb S.

EXAMPLE 9

Desulfurization of n-butane containing 150 ppb S in the form of dimethyl trisulfide was carried out in a manner analogous to that described in Example 2. It was possible to attain a residual sulfur content of less than 5 ppb S, i.e. below the detection limit.

EXAMPLE 10

A propene/propane mixture composed of about 75% propene and about 25% propane and containing 646 ppb S in the form of dimethyl disulfide and dimethyl trisulfide (for gas chromatogram see FIG. 1) was brought into contact with a palladium hydrogenation catalyst at a temperature of 20° C. at a pressure of 15 bar. In doing so, the two above-mentioned sulfur compounds were converted into a multitude of new sulfur-containing compounds of which methyl-propyl sulfide was the main component (gas chromatogram see FIG. 2).

This reaction mixture was desulfurized for 36 h on a zeolite of type X having a content of 10% Ag and 2% Cu, produced in a manner analogous to that described in Example 1, at a temperature of 110° C., a pressure of 10 bar and a WHSV of 20 $h^{-1}$. The propene/propane mixture so obtained had a residual sulfur content of less than 5 ppb S (gas chromatogram see FIG. 3).

Figure 2:
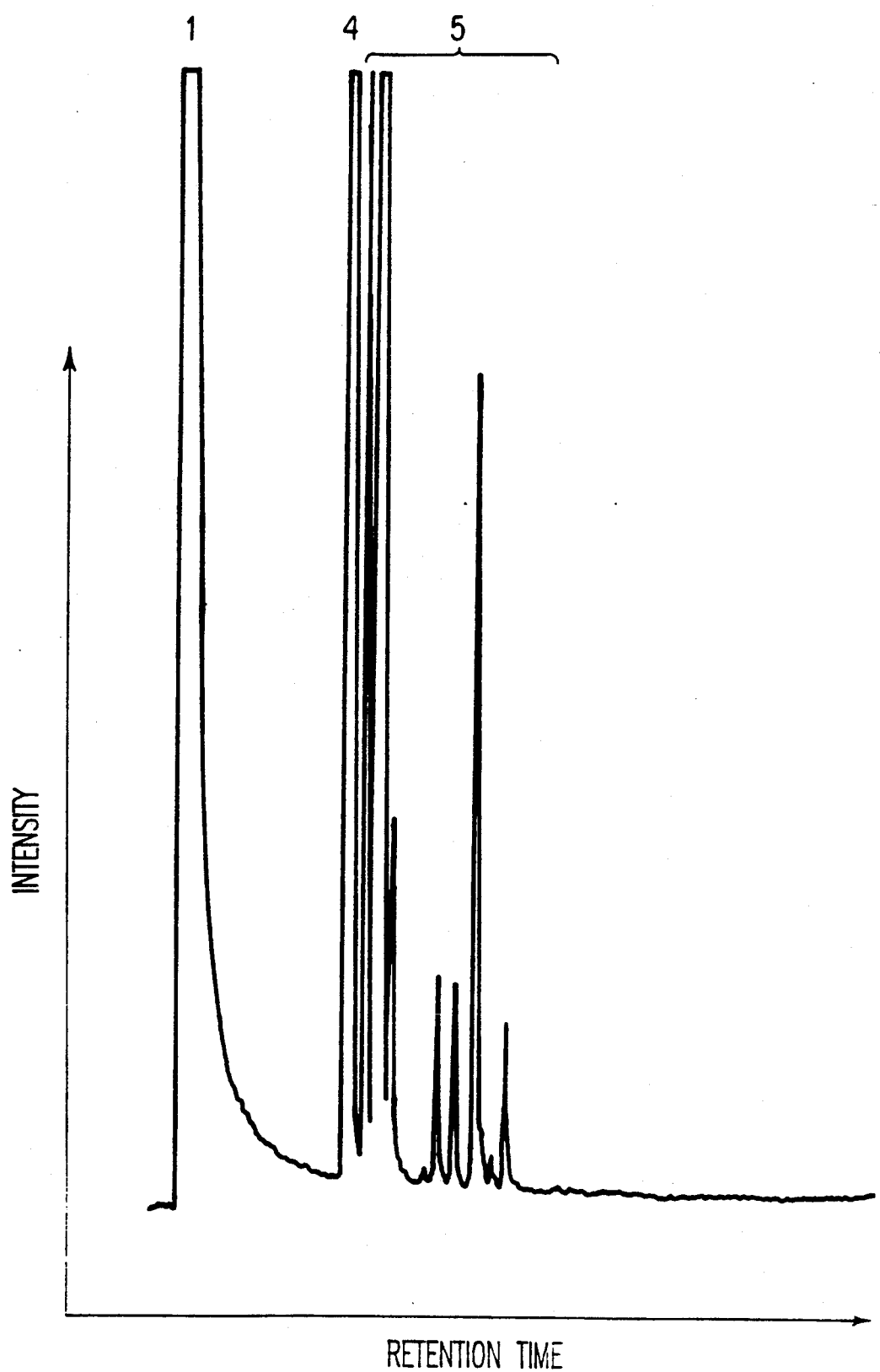
FIG. 2 is a gas chromatogram of the propene/propane material after contact with a hydrogenation catalyst.
Figure 3:
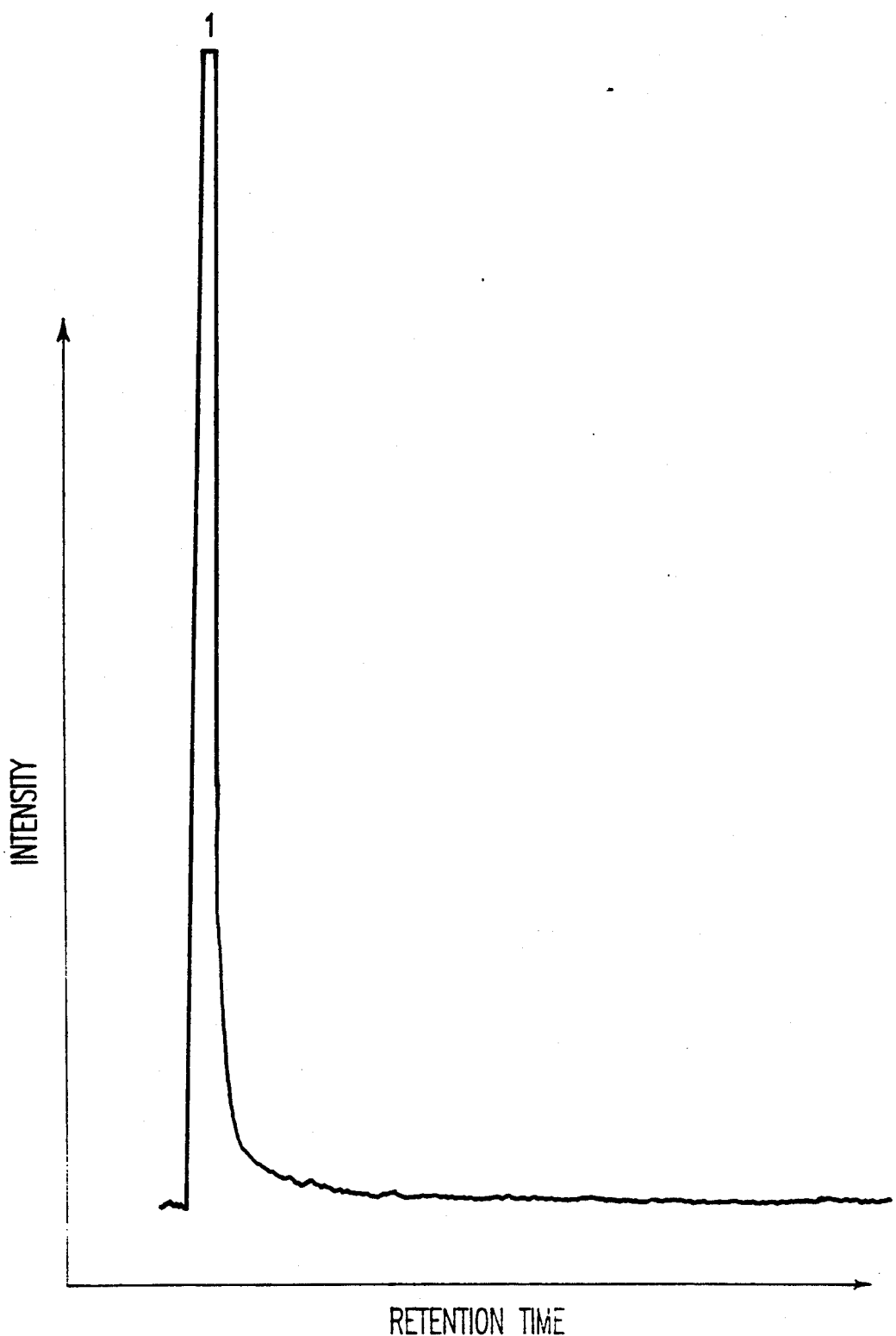
FIG. 3 is a gas chromatogram of the propene/propane material of FIG. 2 after desulfurization over an exchanged zeolite.

Notes on FIGS. 1 to 3

In FIGS. 1 to 3 the results of gas chromatographic analyses are depicted. In each case the peak intensity is plotted as a function of the retention time.

FIG. 1: Gas chromatogram of the propene/propane starting mixture described in Example 10.

FIG. 2: Gas chromatogram of propene/propane mixture after contact with the hydrogenation catalyst as described in Example 10.

FIG. 3: Gas chromatogram of the desulfurized propene/propane mixture as described in Example 10.

The individual peaks in the gas chromatograms were identified as follows:

1 propene/propane
2 dimethyl disulfide
3 dimethyl trisulfide
4 methyl-propyl sulfide
5 various other sulfur compounds

COMPARATIVE EXAMPLE 1

The procedure described by Shcherbina et al., in Obshch. Prikl. Khim., No. 5 (1972), 113–114).

Example 2 was repeated on a sodium zeolite of type X not subjected to ion exchange. After 4 days the same sulfur contents were found in the zeolite bed as in the feed, at a level of about 150 ppb S.

COMPARATIVE EXAMPLE 2

Example 6 of the above referenced Shcherbina et al publication was repeated on a sodium zeolite of type X not subjected to ion exchange. As in comparative Example 1, a complete break-through of methyl-2-butyl sulfide was observed here as well, more particularly at a concentration of about 500 ppb, calculated as S.

COMPARATIVE EXAMPLE 3

According to JP 59/160 584

Example 2 was repeated on activated charcoal serving as the desulfurization agent and having a copper-II-oxide content of 5.5%. After the desulfurization test, the n-butane still contained about 85 ppb S.

COMPARATIVE EXAMPLE 4

According to DD-PS 241 196 and DD-PS 241 197.

Example 6 was repeated on a manganese zeolite of type X having a content of 8% manganese. The n-butane after the desulfurization test contained a high residual sulfur content of 350 ppb in the form of methyl-2-butyl sulfide.

Having now fully described this invention, it will be apparent to one of ordinary skill in the art that many changes and modifications can be made thereto without departing from the spirit or scope of the invention as set forth herein.

We claim:

1. A method of desulfurization of hydrocarbons which contain organic sulfides, disulfides, trisulfides, tetrasulfides, or mixtures of such sulfides in amounts such that the sulfur content of the hydrocarbons is less than 20 ppm by weight of sulfur, said method comprising:

contacting said hydrocarbons containing less than 20 ppm by weight of sulfur with a zeolite containing exchangeable cations in which the exchangeable cations of the zeolites have been completely or partially exchanged with cations of copper, silver, zinc or mixtures thereof.

2. The process according to claim 1, wherein the hydrocarbon is subjected to desulfurization at temperatures of 50° to 350° C.

3. The process according to claim 1, wherein the hydrocarbon is subjected to desulfurizaton at pressures of 1 to 200 bar.

4. The process according to claim 1, wherein the sulfur containing hydrocarbon contains 1 to 20 carbon atoms.

5. The process according to claim 1, wherein said zeolite has a particle size of from 0.01 to 5 mm.

6. The process according to claim 1, wherein the hydrocarbon is subjected to desulfurization at temperatures of 50° to 130° C.

7. The process according to claim 1, wherein the hydrocarbon is subjected to desulfurization at pressures of 1 to 50 bar.

8. The process according to claim 1, wherein the hydrocarbon is contacted with said zeolite at a weight hourly space velocity of 0.05 to 100 $hr^{-1}$, wherein said weight hourly space velocity is defined as (the amount of starting material in kg)/(amount of zeolite in kg)×(time to treat the starting material in hours)).

9. The process according to claim 1, wherein the content of the zeolite with respect to copper, silver or zinc, respectively, amounts to at least 2% by weight.

* * * * *